United States Patent
Pryne et al.

(10) Patent No.: US 10,245,343 B2
(45) Date of Patent: Apr. 2, 2019

(54) SCENTED WAFER

(71) Applicant: American Felt & Filter Company, New Windsor, NY (US)

(72) Inventors: Scott H. Pryne, New Windsor, NY (US); Mike Horaz, Cornwall, NY (US); Mark A. Pryne, Cornwall, NY (US)

(73) Assignee: AMERICAN FELT & FILTER COMPANY, New Windsor, NY (US)

( * ) Notice: Subject to any disclaimer, the term of this patent is extended or adjusted under 35 U.S.C. 154(b) by 297 days.

(21) Appl. No.: 14/338,761

(22) Filed: Jul. 23, 2014

(65) Prior Publication Data

US 2016/0022859 A1 Jan. 28, 2016
US 2016/0206770 A9 Jul. 21, 2016

Related U.S. Application Data

(60) Provisional application No. 61/869,234, filed on Aug. 23, 2013, provisional application No. 61/969,305, filed on Mar. 24, 2014, provisional application No. 62/000,029, filed on May 19, 2014.

(51) Int. Cl.
  *A61L 9/12* (2006.01)
  *A61L 9/012* (2006.01)
  *A01M 1/20* (2006.01)
  *A61L 9/03* (2006.01)

(52) U.S. Cl.
  CPC ............. *A61L 9/12* (2013.01); *A01M 1/2061* (2013.01); *A61L 9/012* (2013.01); *A61L 9/03* (2013.01)

(58) Field of Classification Search
  CPC ... A61L 9/12; A61L 9/122; A61L 9/03; A61L 9/012; A01M 1/2061
  USPC .............................. 239/34–60; 392/392, 390
  See application file for complete search history.

(56) References Cited

U.S. PATENT DOCUMENTS

| | | | |
|---|---|---|---|
| 4,722,477 A * | 2/1988 | Floyd .................. | A01M 31/008 224/267 |
| 5,007,529 A | 4/1991 | Spector | |
| 5,246,603 A * | 9/1993 | Tsaur ..................... | C11D 3/001 510/516 |
| 5,800,897 A * | 9/1998 | Sharma ................... | A61L 9/042 239/53 |
| 7,132,084 B1 | 11/2006 | Roumpos | |
| 7,670,566 B2 * | 3/2010 | Adair .................. | A01M 1/2077 239/34 |
| 7,713,488 B2 | 5/2010 | Harris et al. | |
| D678,496 S | 3/2013 | Browder | |
| 8,412,029 B2 | 4/2013 | Browder et al. | |
| 8,716,632 B1 * | 5/2014 | Pesu .................... | H05B 1/0269 219/433 |
| 2003/0150467 A1 | 8/2003 | Robinson | |

(Continued)

*Primary Examiner* — Alexander M Valvis
*Assistant Examiner* — Tuongminh N Pham
(74) *Attorney, Agent, or Firm* — Nixon & Vanderhye PC

(57) ABSTRACT

A scented wafer having a body formed of a heat resistant fibrous material having a predetermined porosity resulting from a selected denier and length of fibers. A scented material is impregnated into the body material and is constructed to melt and release a scent when exposed to heat at a predetermined temperature for aromatherapy, insect repellant, wild life attractant, medicinal use, deodorant and odor control, perfume release, or any other desired or suitable purpose. The body material does not melt at the predetermined temperature.

15 Claims, 4 Drawing Sheets

(56) References Cited

U.S. PATENT DOCUMENTS

| | | | |
|---|---|---|---|
| 2004/0217188 A1* | 11/2004 | McEwen | A01M 1/2044 239/44 |
| 2006/0102737 A1 | 5/2006 | Harmon et al. | |
| 2006/0283970 A1 | 12/2006 | Faires et al. | |
| 2008/0099576 A1 | 5/2008 | Hart | |
| 2008/0116197 A1 | 5/2008 | Penman et al. | |
| 2008/0130266 A1 | 6/2008 | DeWitt et al. | |
| 2008/0179424 A1 | 7/2008 | Cheung | |
| 2011/0290908 A1* | 12/2011 | Tranzeat | A01M 1/2033 239/44 |
| 2012/0183280 A1 | 7/2012 | Kowalec et al. | |

* cited by examiner

SCENTED WAFER

CROSS REFERENCE TO RELATED APPLICATIONS

The present application claims the priority of Provisional Application No. 61/869,234 filed on Aug. 23, 2013, Provisional Application No. 61/969,305 filed on Mar. 24, 2014 and Provisional Application No. 62/000,029 filed on May 19, 2014.

BACKGROUND OF THE INVENTION

1. Field of the Invention

The present invention relates to a scented wafer and, more particularly, to a wafer that is impregnated with a scented material that emits a scent when heated that can be used for any suitable purpose, for example, aromatherapy, insect repellant, wild life attractant, medicinal uses, deodorants and odor control, perfume release and other desired or suitable purposes.

2. Description of the Prior Art

Various devices are currently used to emit scents in a surrounding area. For example, scented candles may be burned or candle tarts may be heated and melted to emit a scent. In the case of a candle, there is a safety hazard resulting from an open flame.

In the case of a candle tart, it turns to liquid when heated and forms a pool that emits a fragrance. The pool is in the form of a hot liquid and thus may spill and result in a burn to the user or damage to a supporting surface.

A need has arisen, therefore, for a new and improved device for emitting a scent when heated that is not subject to the disadvantages of a candle or candle tart. The scented wafer of the present invention meets this need.

BRIEF SUMMARY OF THE INVENTION

The wafer of the present invention may be of any suitable size or shape and comprises a heat resistant body formed of any suitable material that is constructed for holding, flow, capillary effect and release of fragrant scents or other scents to be used for any desired or suitable purpose, such as aromatherapy, insect repellant, wild life attractant, medicinal uses, deodorants and odor control, perfume release. The term "scent" as used herein is intended to cover any material that will release a detected or undetected vapor when heated for any useful or desired purpose.

The body of the wafer is impregnated in any suitable manner with a suitable or desired scented wax or other liquid scent that will melt or vaporize when exposed to heat to emit the scent in the surrounding area. The rate of release of the scent is controlled by the porosity and capillary function of the body material as well as the temperature of the applied heat, and can be varied by the use of fiber denier and length blends in the body material. For example, finer fibers will create tighter structures to obtain a slow release of the scented material when heated and a greater surface area for pickup and holding of the scented material. Larger fibers will create more coarse and open structures for a quicker release of the scented material when heated and will have less surface for initial pickup and holding of the scented material The body of the wafer is formed of a heat-resistant material that does not melt when the scented material impregnated therein is heated and melted. The body material may soften during heating of the scented material but retains its structural integrity and will thereafter harden when cooled so that the wafer can be reused. When depleted of scented material, the wafer may in some circumstances be impregnated again with a scented material so that it can be reused.

If the wafer is to be used with an open flame, the body material and fibers will be of a flame retardant material. If a conventional plate warmer or similar heater is to be used, the body material and fibers can be of a material that does not melt at the temperature of the plate warmer or heater.

DETAILED DESCRIPTION OF THE INVENTION

Figure 1:
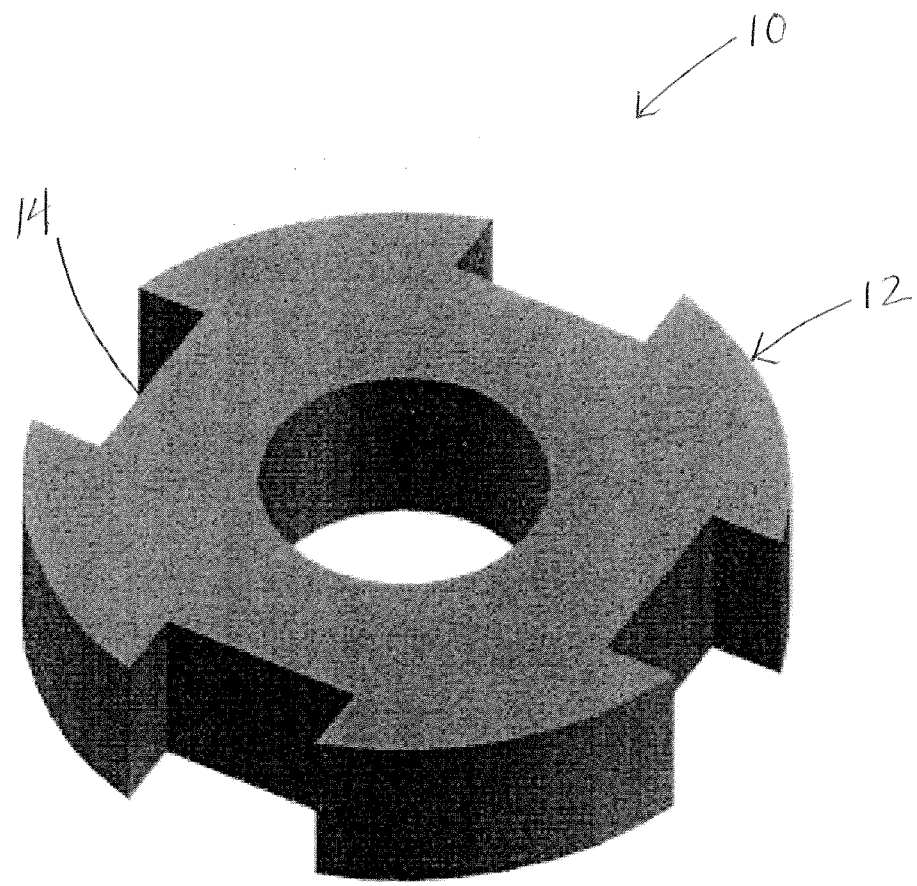
FIGS. 1, 1A and 1B are perspective views of different illustrative embodiments of a wafer that is constructed in accordance with the principles of the present invention. These views are merely illustrative for the reason that the wafer may be of any suitable size or shape.

FIG. 1 shows a wafer 10 of the present invention that may be of any suitable size or shape, and comprises a body 12 formed of any suitable heat-resistant material having fibers that are constructed for holding, flow, capillary effect and release of a scent to be used for any suitable or desired purpose.

The body 12 of the wafer is impregnated in any suitable manner with a suitable scented wax or other liquid scent that will melt or vaporize when exposed to heat to emit the scent in a surrounding area. The rate of release of the scent is controlled by the porosity and capillary function of the body material, as well as the temperature of the applied heat, and can be varied by the use of fiber denier and length blends in the body material. For example, finer fibers will create tighter structures to obtain a slow release of the scented material when heated and a greater surface area for pick up and holding of the scented material. Larger fibers will create more coarse and open structures for a quicker release of the scented material when heated and will have less surface for initial pick up and holding of the scented material. As an illustrative example, fibers may range from 0.5 micron to 25 denier and from lengths of 1/16 inch to 10 inches.

The body 12 of the wafer is formed of a suitable material that does not melt when the scented material impregnated therein is heated and melted. The body material may soften during heating of the scented material but retains its structural integrity and will thereafter harden when cooled so that the wafer can be reused. In some cases, when the wafer is depleted of scented material, it may be impregnated again with a desired scented material so that it can be reused.

Figure 2A:
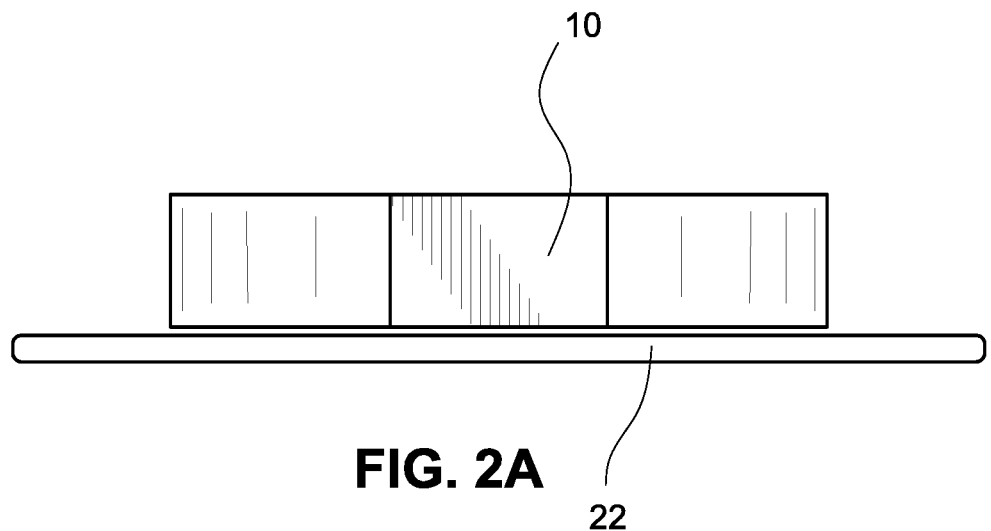
FIG. 2A is a side elevational view of a scented wafer of the present invention being heated by a conventional plate warmer.
Figure 2B:
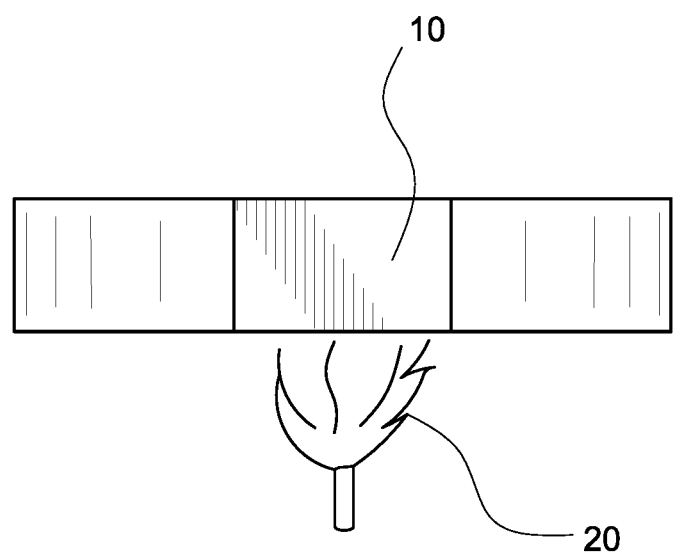
FIG. 2B is a side elevational view of a scented wafer of the present invention being heated by an open flame.

If the wafer 10 is to be used with an open flame, 20 as shown in FIG. 2B, the body material and fibers will be of a flame retardant material. Fibers such as but not limited to meta and para aramids, modacrylics, flame retardant polyesters, as well as oxidized polyacrylonitrile carbonized fibers may be used because they are inherently flame retardant. Glass fibers and blends of glass fibers can also be used in higher temperature applications. In general, the wafer may be comprised of flame retardant fibers such as modacrylics, flame retardant polyesters, Nomex, Kevlar, PBO, PBI, Meta Aramids and Para Aramids, glasses, silicas, polyacrylonitrile or carbon, blends of these materials or any other suitable materials.

If conventional plate warmer 22 shown in FIG. 2A or similar heater is to be used, the body material may be formed of any suitable material such as synthetics or blends of suitable materials that will resist melting at temperatures ranging from about 130-140° F., or any other desired temperature range.

As illustrative examples, the body 12 may be formed of any nonwoven, woven, meltblown, spunbond, thermo bonded, extruded or resin bonded material comprised of any natural or synthetic blend and varied deniers of fibers, or of any suitable capillary wicking material. The density can be adjusted so that its porosity will be suitable for holding and release of any desired or suitable scent or scents.

The body 12 may have any suitable or desired shape, such as flat form, two dimensional, three dimensional or multi-dimensional. Also, the body 12 may be formed in any suitable or desired manner, such as pressed and cut, pressed cavity formed and cut or extruded formed and cut.

Any suitable scented wax or other fragrance or scented material may be used. Specific illustrative examples of suitable waxes and fragrances or scents are as follows:

Waxes

Animal and plant based waxes
(all natural waxes)
Petroleum based wax
Synthetic based wax Fragrances or Scents Oil based, water based and alcohol based which can be derived from natural and/or synthetic ingredients.
The amount of fragrance or scent can range, e.g., from 1% to 100% but typically falls in the 10%-30% range by weight FIGS. 1A and 1B illustrate wafers 110 and 210 having bodies 112 and 212, respectively, that have different shapes from the wafer 10 shown in FIG. 1 and are formed in the same manner as the wafer 10.

Figure 1A:
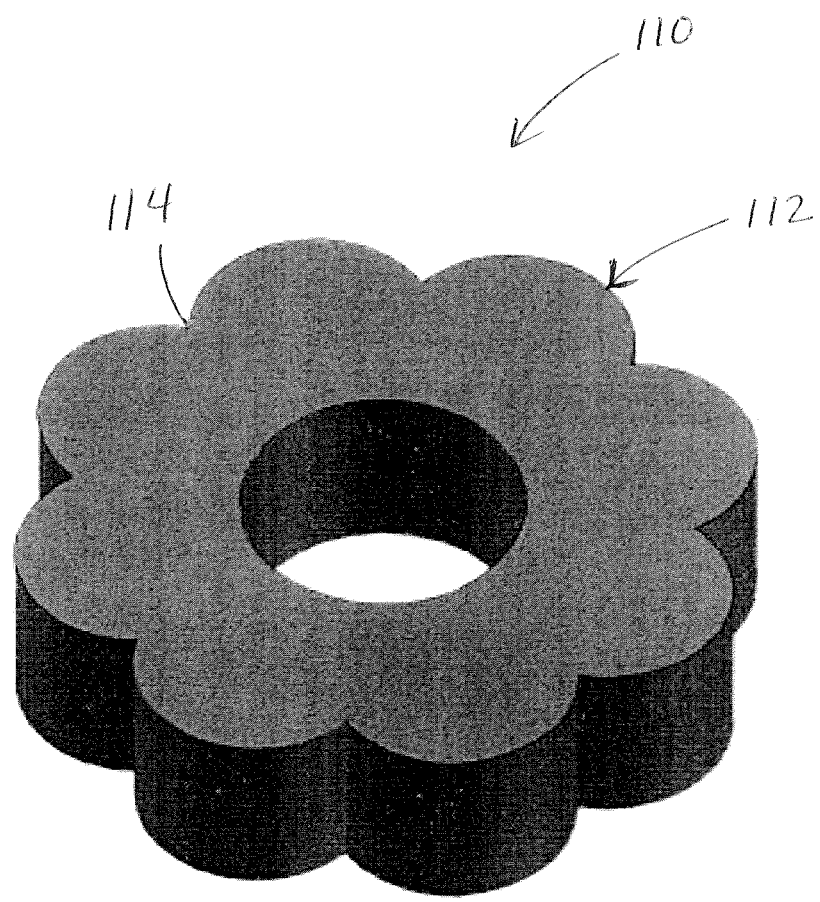
Figure 1B:
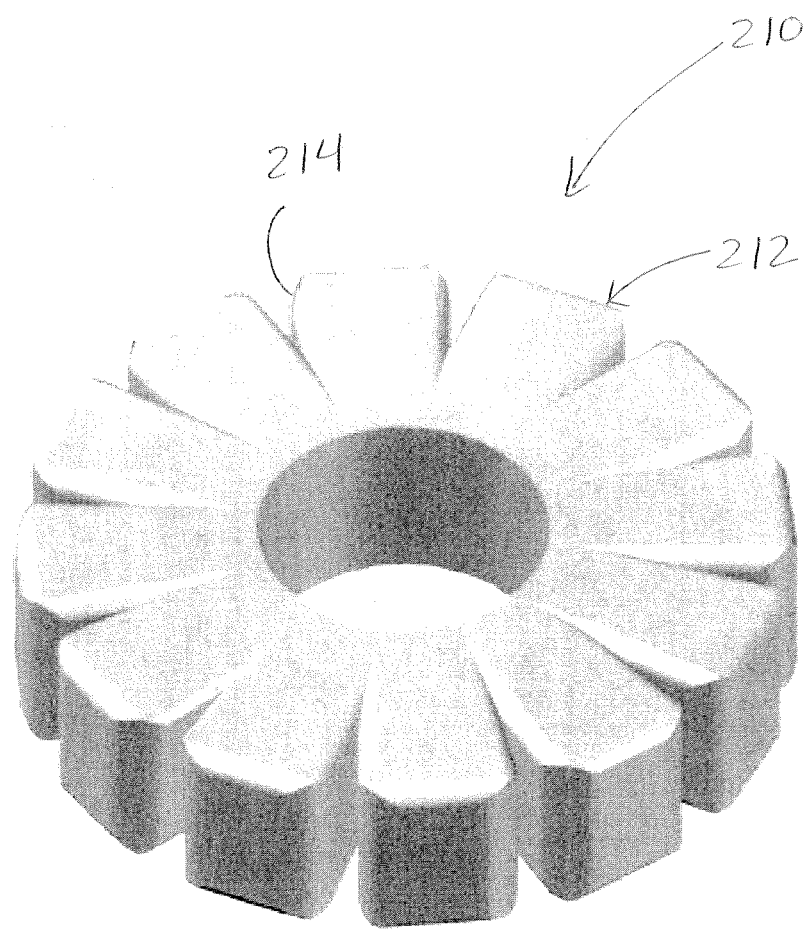

As shown in FIGS. 1, 1A and 1B, the body of the wafer may be formed with numerous edges and grooves 14, 114, 214 to create a greater surface area for emission of the scent.

A general comparison of the amount of wax and fragrance used by a conventional wax tart and different illustrative embodiments of the scented wafer of the present invention is as follows:

Conventional Wax Tart
6 tarts at 12 grams=72 grams total
Fragrance or scent (15% load)—6 tarts at 1.8 grams=10.8 grams total
Scented Wafer (Single Large Fiber Wafer)
Total weight—25 grams
Fragrance or scent (25% load)—6.25 grams
Wax—18.75 grams
Scented Wafer (6 Mini Fiber Wafers)
6 wafers at 8 grams=48 grams total
Fragrance or scent (15% load)—6 wafers at 1.2 grams=7.2 grams total
Wax—6 wafers at 6.8 grams=40.8 grams total It is apparent, therefore, that different embodiments of the scented wafer of the present invention can use less fragrance or scent and wax than a conventional wax tart.

The scented wafer 10 of the present invention possesses many advantages over conventional scented candles, wax tarts or other known scent releasing devices, some of which are as follows:

1. A significantly longer life span;
2. Can be easily reused after a heating cycle;
3. Very safe to use since there is no open flame or exposed hot melted wax;
4. Can be constructed with various fibrous structures to control the rate of release of the scented material impregnated therein;
5. Uses less wax and fragrance to create a desired scent;
6. Can be easily and safely stored;
7. Is inexpensive to manufacture;
8. Can be created with numerous surfaces to present a large surface area for emission of scent;
9. Can be constructed of different fibrous materials depending on the scented material and on the heat source used to melt or vaporize the scented material impregnated therein; and
10. Can be used to release a scent for any suitable or desired purpose.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A scented wafer for emitting a scent to a surrounding open environment,
    said scented wafer being uncovered to present a large surface area for emission of scent to the surrounding open environment, and comprising a body material formed of a heat-resistant fibrous material having a predetermined porosity resulting from a selected denier and length of fibers; and
    a scented material impregnated into the body material and constructed to melt and release a scent when exposed to heat of a predetermined temperature that exceeds the temperature of the surrounding open environment and a melting point of the scented material;
    wherein the body material retains structural integrity and does not melt at the predetermined temperature to facilitate the reuse or replacement of the wafer, and
    the body is formed with numerous edges and grooves to create a large surface area for emission of the scented material when heated and melted.

2. The scented wafer of claim 1 wherein the body material is selected from a group comprising nonwoven, woven, meltblown, spunbond, extruded thermal bonded, extruded chemical bonded, resin bonded nonwovens, pulp and cellulose composite materials.

3. The scented wafer of claim 2 wherein the body material is comprised of a natural or synthetic blend and varied denier of fibers.

4. The scented wafer of claim 1 wherein the fibers comprise a synthetic material.

5. The scented wafer of claim 1 wherein the fibers comprise a natural material.

6. The scented wafer of claim 1 wherein the fibers comprise glass.

7. The scented wafer of claim 1 wherein the fibers comprise a pulp based material.

8. The scented wafer of claim 1 wherein the fibers comprise organic starch derivative material.

9. The scented wafer of claim 1 wherein the fibers are polyester with a high degree of moisture regain and temperature and chemical resistivity.

10. The scented wafer of claim 1 wherein the scented material is wax.

11. The scented wafer of claim 1 wherein the fibers are of a fine structure and small size so as to create a tight structure in the body material for a slow release of scented material therefrom when it is heated and melted.

12. The scented wafer of claim 1 wherein the fibers are of a coarse structure and large size so as to create a coarse and open structure in the body material for a quick release of scented material therefrom when it is heated and melted.

13. The scented wafer of claim 1 wherein the fibers range from 0.5 denier to 25 denier and from lengths of 1/16 inch to 10 inches.

14. The scented wafer of claim 1 wherein the body material is felt.

15. The scented wafer of claim 1 wherein the body material will harden when cooled so that it can be reused when it still contains scented material impregnated therein.

\* \* \* \* \*